(12) United States Patent
Zhu

(10) Patent No.: US 6,974,482 B2
(45) Date of Patent: Dec. 13, 2005

(54) IMPLANTABLE ORTHOPEDIC PROSTHESIS WITH TEXTURED POLYMERIC SURFACES

(75) Inventor: Mengke Zhu, Austin, TX (US)

(73) Assignee: Zimmer Austin, Inc., Austin, TX (US)

( * ) Notice: Subject to any disclaimer, the term of this patent is extended or adjusted under 35 U.S.C. 154(b) by 12 days.

(21) Appl. No.: 10/302,069

(22) Filed: Nov. 22, 2002

(65) Prior Publication Data

US 2004/0102854 A1    May 27, 2004

(51) Int. Cl.[7] .............................................. A61F 2/32
(52) U.S. Cl. .................................................. 623/22.11
(58) Field of Search ........................... 623/22.11–22.2, 623/22.4–23.3

(56) References Cited

U.S. PATENT DOCUMENTS

| | | | |
|---|---|---|---|
| 4,164,794 A | | 8/1979 | Spector et al. |
| 4,199,864 A | | 4/1980 | Ashman |
| 5,458,653 A | * | 10/1995 | Davidson .................. 623/23.36 |
| 5,507,832 A | * | 4/1996 | Michielli et al. ......... 623/23.37 |
| 5,874,123 A | * | 2/1999 | Park .......................... 427/2.24 |
| 5,876,446 A | * | 3/1999 | Agrawal et al. .......... 623/23.61 |
| 5,879,400 A | | 3/1999 | Merrill et al. |
| 6,033,582 A | * | 3/2000 | Lee et al. ...................... 216/37 |
| 6,582,470 B1 | * | 6/2003 | Lee et al. ................. 623/23.55 |
| 2001/0039454 A1 | * | 11/2001 | Ricci et al. ................. 623/23.5 |

* cited by examiner

Primary Examiner—Eduardo C. Robert
(74) Attorney, Agent, or Firm—Greer, Burns & Crain, Ltd.; Jonathan D. Feuchtwang

(57) ABSTRACT

Implantable prostheses fully or partially formed of polymer having a textured or porous outer surface. The surface permits and encourages osteogenesis into the prosthesis and enables it to become firmly and permanently anchored into surrounding bone. The prostheses include a femoral hip stem formed of a metallic core and a polymeric proximal body with a textured or porous surface formed from a laser texturing, machining, or grit blasting.

19 Claims, 5 Drawing Sheets

IMPLANTABLE ORTHOPEDIC PROSTHESIS WITH TEXTURED POLYMERIC SURFACES

FIELD OF THE INVENTION

The disclosure herein generally relates to implantable orthopedic prostheses and, more particularly, to polymeric implants with textured or porous outer surfaces adapted to engage bone.

BACKGROUND OF THE INVENTION

Two main techniques are commonly used to fix an implantable orthopedic prosthesis to bone: Techniques using bone cement, and techniques pressing the implant into position. During the former technique, bone cement (typically PMMA, or polymethylmethacrylate) is applied in a dough-like state as a grouting agent between the bone and the implant. The cement flows around the contours of the osteotomy and the implant and into the interstices of cancellous bone. Upon hardening, the cement forms a mechanical interlock between the bone and the outer surface of the implant. In effect, no bone growth into the surface of the implant occurs since cement is used to hold the implant in place.

Although bone cement gives good initial fixation, it has some disadvantages. As one example, the bond between the bone and implant can weaken over time and cause complications. Further, implants affixed with cement can subside after the cement hardens and also cause unwanted problems.

During the technique of pressing the implant into bone, no bone cement is used. Rather the implant is press-fit into a prepared bone cavity that closely approximates the shape of the implant. Long term stability of press-fit implants requires bone to form an interlock with the outer surface of the implant.

Currently, all porous coatings or textured surfaces of orthopedic implants are fabricated using mainly metallic materials and are on metallic substrates. Therefore, the contemporary porous coatings or textured surfaces of orthopedic implants have a much higher elastic modulus than surrounding bone. As a result of this disparity in elastic modulus, bone tissues are likely fractured or crashed because of the micro-motion and press-fit at the bone-implant interface.

Conventional press-fit prosthesis often provide inconsistent long-term fixation to bone because of inadequate interfacial osteogenesis (i.e., bone growth directly to the outer surface of the implant). As such, much effort and research have been devoted to understanding how bone grows into these surfaces; and how these surfaces can be modified to encourage such growth. In particular, much research has been directed toward bone growth into textured or porous surfaces adapted to engage bone.

Bone growth into porous orthopedic implants is generally a two stage phenomenon. In the first stage and immediately after implantation, the pores or outer textured surface of the porous component fills with a blood clot that begins to organize. Here, fibroblasts appear in the clot region and fibrogenesis occurs. Loose connective tissue and capillaries soon replace the clot. At this point, pre-osteoblasts begin to appear in the peripheral pores of the implant. These cells can become osteoblasts or chondroblasts depending upon the environment. If the original pore size of the implant is too small or if the porous structure has been distorted by applied loads, one or more of the above sequence of events can be interrupted or hampered. For example, a smaller pore size (<90 $\mu$m) generally leads to the ultimate formation of fibrous tissue, not bone in the implant.

In the second stage, after bone has filled the pores of the implant, the bone begins to remodel. Here, spicules in the implant that experience uniform stress tend to thicken while those spicules that experience no stress or excessive stress (stress concentration) tend to become resorbed.

During this stage, the material properties of the implant are very important. In particular, implants formed from metal and ceramic can have a distinct disadvantage. For example, the modulus of metals and ceramics is so high that the implants do not sufficiently deform under the applied loads. The implant thus does not adequately spread load to surrounding bone (known as "stress-shielding"), and resorption can occur. Further, bone spicules in these porous implants do not experience sufficient loads to thicken. Bone trabeculae in the higher modulus porous materials tend to thin, a situation that also can lead to resorption.

From this discussion, an important conclusion can be drawn: The biomechanical environment established by the implant material and the geometry of the porous substrate can have a profound effect on osteogenesis or osteointegration at the bone-implant interface. Not surprisingly, much effort has been directed toward engineering polymeric coatings for use with implants. For example, some prior implantable prosthetic devices have been coated with porous bio-engineered thermoplastic materials. U.S. Pat. No. 4,164,794, entitled "Prosthetic Devices Having Coatings of Selected Porous Bioengineering Thermoplastics," teaches a prosthesis having a thermoplastic coating to encourage bone growth into the surface.

Efforts also have been directed toward forming implants entirely of polymeric materials. Polymeric implants can have excellent characteristics for orthopedic, dental, and maxillofacial applications. The transmission of stress to bone in some of these implants more closely mimics the physiological, natural biomechanical environment. U.S. Pat. No. 4,199,864, entitled "Endosseous Plastic Implant Method," for example, teaches a cast polymeric implant having a porous surface to encourage bone growth. The porous surface was fabricated through polymerization of a powdered polymer-liquid monomer mixture. The prior art, then, has directed much effort to coating metallic implants with a polymer or forming implants entirely from polymers. At the same time, much research has been devoted to bone growth into metals and polymers alike.

It therefore would be advantageous to provide an implantable orthopedic prosthesis that was formed at least partially from a polymer having a porous or textured outer surface to promote osteogenesis.

SUMMARY

The present invention is directed to implantable prosthetic devices fully or partially formed of polymer having a textured or porous bone engaging outer surface. The surface permits and encourages bone growth or osteogenesis into the prosthesis and enables it to become firmly and permanently anchored into surrounding bone.

Prostheses of the present invention are intended to be press-fit into a prepared bone cavity. Preferably then, no cement is used. As one important advantage of the present invention, the textured or porous surface is not applied as a coating to the prosthesis or fabricated during the formation of the polymer or polymeric structure. Rather, any one of or combination of several surface texturing techniques is used to form the textured or porous surface. These techniques include grit blasting, laser texturing, and machining (such as cutting, drilling, knurling, milling, and combinations of these techniques). Preferably, ultra high molecular weight polyethylene, UHMWPE, is used to form the polymeric components.

The porous surface layer can also be coated, doped, or the like with another media to enhance bone bonding properties between the prosthesis and surrounding bone. Plasma sprayed titanium, hydroxyapatite, or growth agents (such as BMPs), for example, can be added or applied to the bone engaging surface.

One embodiment of the present invention includes an orthopedic implant and, specifically, a femoral hip stem and accompanying prosthetic acetabulum. The femoral hip stem is formed of a metallic core with a polymeric proximal body. The acetabulum is formed entirely of polymer. The outer surface or bone engaging surface of the proximal body and acetabulum are texturized with one or more of the noted techniques. These surfaces are adapted to induce bone growth into the surface.

In this embodiment, since the proximal body and acetabulum are entirely formed of polymer, the elastic modulus of the implant more closely matches the natural elastic modulus of surrounding bone. The minimization of the elastic modulus mismatch between the implant and bone reduces the degree of bone resorption consistent with traditional metallic implants.

Another embodiment of the present invention includes an orthopedic implant and, specifically, an all-polymeric tibial articulating component

BRIEF DESCRIPTION OF THE DRAWING FIGURES

DETAILED DESCRIPTION

Figure 1:
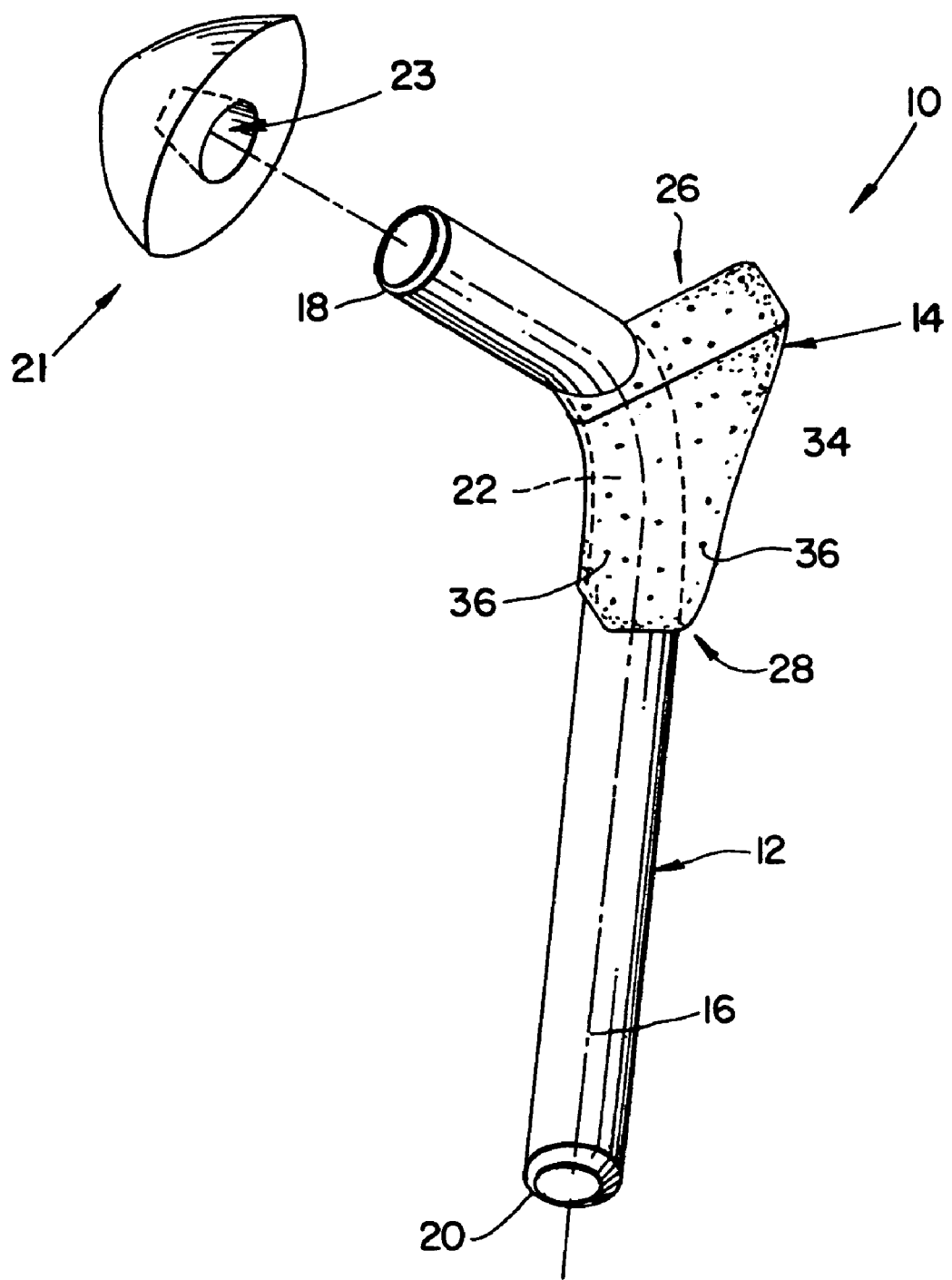
FIG. 1 is an isometric view illustrating an embodiment of an orthopedic femoral hip implant including a core, a proximal body, and a ball.

Looking to FIG. 1, an implantable orthopedic femoral hip implant 10 is shown. Implant 10 includes a solid metal core 12 and a proximal body 14 formed entirely of a polymer. The metal core 12 is formed as an elongated shaft or body and extends from a first or proximal end 18 to a second or distal end 20. A contoured, longitudinal axis 16 extends down the center of the shaft.

Figure 2:
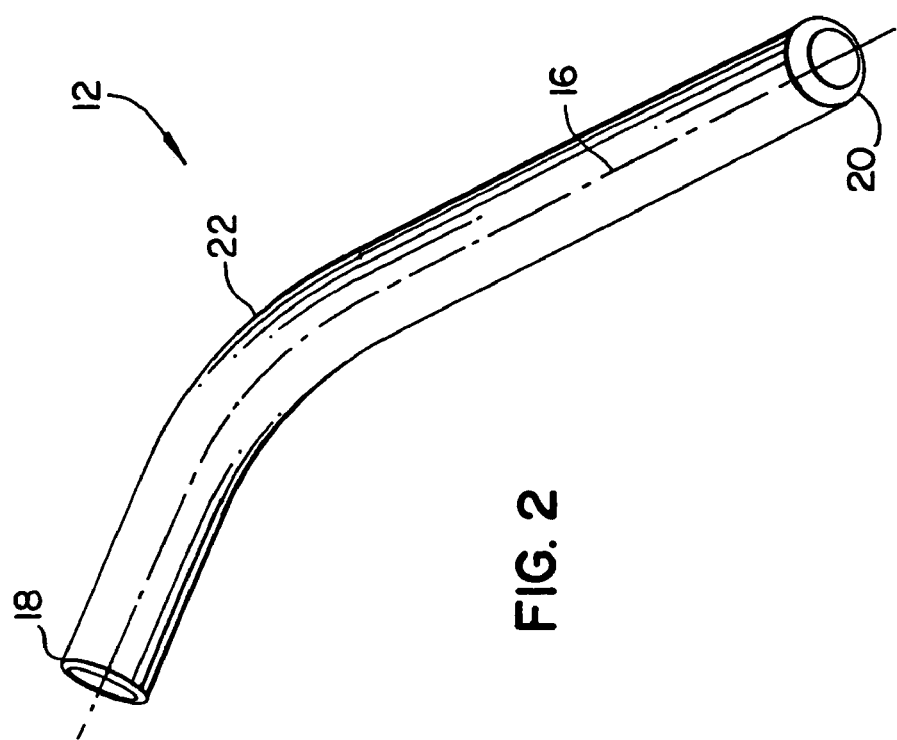
FIG. 2 is an isometric view illustrating an embodiment of the core.

Looking also to FIG. 2, the first end 18 is tapered and adapted to matingly engage and connect to a femoral bait or head 21. The head 21 includes a tapered bore or recess 23 adapted to receive and engage first end 18.

The second end 20 is rounded to facilitate insertion into the intramedullary canal at the proximal end of a femur. Between the first and second ends 18 and 20, respectively, the metal core 12 has a proximal portion 22 that connects to the proximal body 14. The proximal portion 22 may have a particular surface finish and geometry for connecting or bonding with the proximal body 14. A plethora of existing art teaches how to bond or connect metal to polymers. Those skilled in the art will appreciate and know these teachings.

Figure 3:
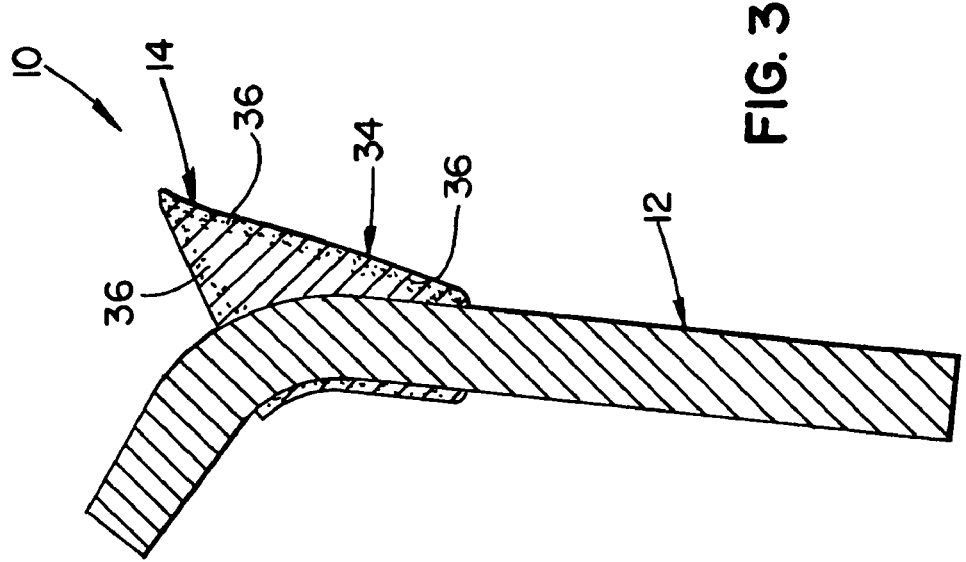
FIG. 3 is a cross-sectional view of the hip implant of FIG. 1.
Figure 4:
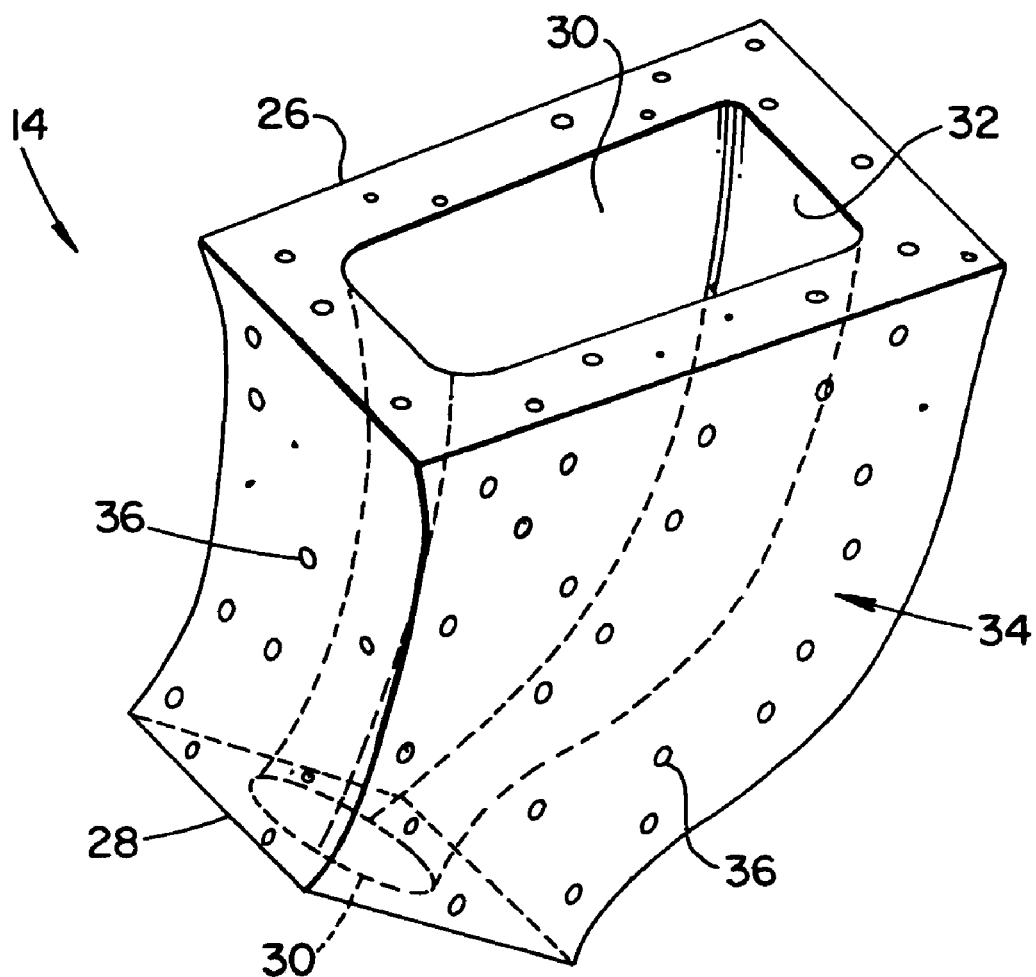
FIG. 4 is an enlarged isometric view illustrating an embodiment of a proximal body.

As best shown in FIGS. 1, 3, and 4, the proximal body 14 is provided to fit into an intramedullary canal of the proximal end of a resected femur. As shown, the proximal body extends from a first or proximal end 26 to a second or distal end 28. A passage 30 is formed through the body and extends from the first end 26 to the second end 28. The passage 30 is shaped to connect to the proximal portion 22 of the metal core 12.

The proximal body 14 also has an outer surface 34 that is textured or porous 36. The porous or textured surface can have a wide range of physical parameters, and preferably this surface covers substantially all the outer surface of the proximal body. The parameters of the porous or textured surface should be compatible with and conducive for the ingrowth of cancellous and cortical bone spicules. In the preferred embodiment, the surface has the following parameters:

(1) a surface textured thickness from about 0.05 mm to about 5 mm (see FIG. 3, illustrating the penetration of the pores into the proximal body);

(2) an average pore diameter from about 40 µm to about 1000 µm;

(3) a porosity ranging from about 40% to 65%;

(4) pore interconnections having average diameters of greater than about 50 microns; and (5) pore geometry, connectivity, and distribution that are random and variable depending upon the method of fabrication and the application.

The parameters of the polymer and textured surface should preferably enable stresses applied on the musculoskeletal system to be transferred to bone spicules within the pores and maintain sufficient load and pore stability to promote irreversible ossification with the prosthesis.

Figure 5:
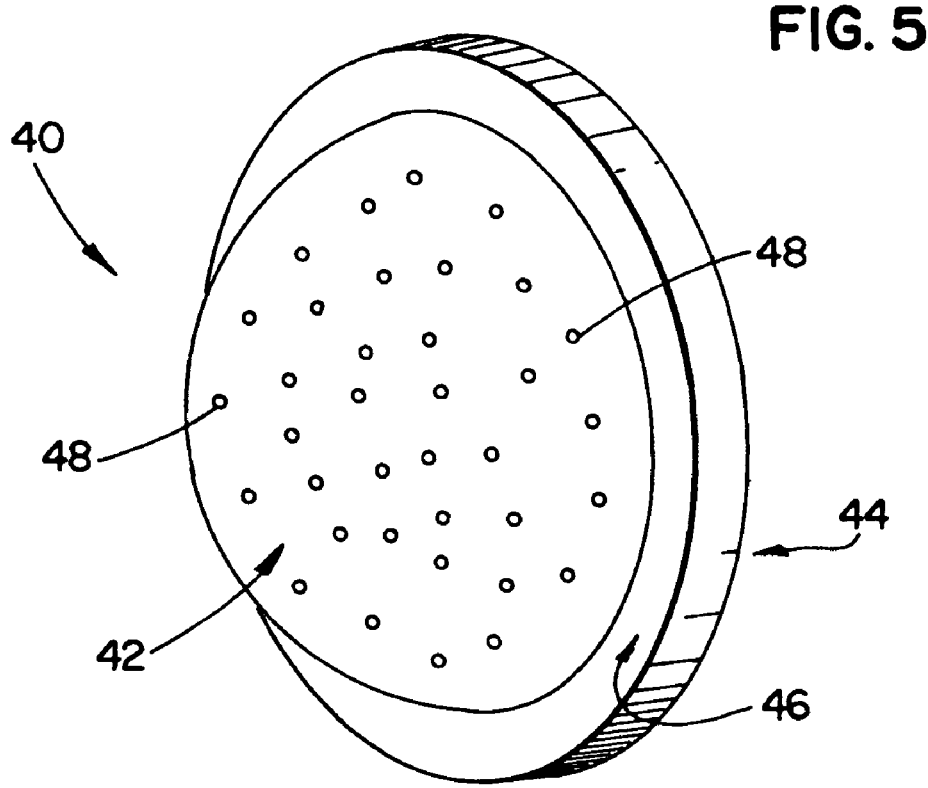
FIG. 5 is another embodiment of the invention illustrating a polymeric acetabulum.

One skilled in the art will appreciate that the textured or porous surface of the present invention can be utilized on a variety of implantable medical devices. FIG. 5 shows one such alternate embodiment as an acetabular insert 40. The insert is formed as a shell and is configured to fit in the acetabulum of a patient, integrate with surrounding bone, and remain in position without the use of any bone cement.

The shell is generally shaped as a hemispherical cup defined by an outer hemispherical surface or bone engaging surface 42 of an inner hemispherical surface or articulating surface 44 having centers that lie on a common axis. The inner and outer surfaces define a shell wall having an annular rim 46. As discussed with reference to the proximal body in FIG. 1, the outer surface (or bone engaging surface) is porous or textured 48 that, preferably, covers substantially all the outer surface. The inner surface is smooth and adapted to articulate with the prosthetic head or ball 21 of the femoral hip implant 10 (FIG. 1).

It is important to note that the outer surface 42 directly contacts and engages bone. As such, a separate shell is not required. Such shells are typically constructed of solid titanium metal or titanium alloy and have a porous coating on the external surface to engage bone. By contrast, the bone engaging or outer surface 42 is textured or porous; and such a shell is not needed. The inner surface 44 is adapted to serve as the articulating surface and thus receives the head or ball 21 of the femoral hip stem (FIG. 1).

Figure 6:
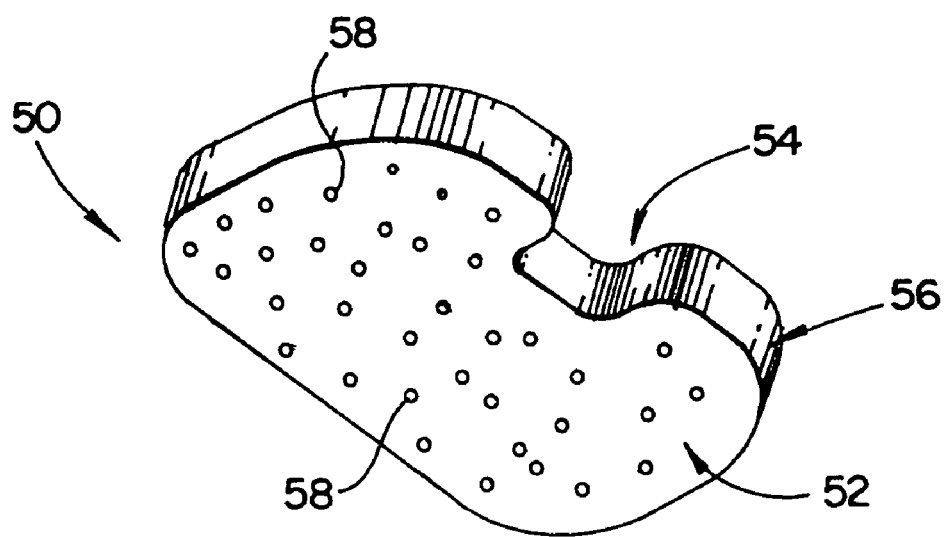
FIG. 6 is another embodiment of the invention illustrating a polymeric tibial insert.

FIG. 6 shows yet another alternate embodiment as a tibial insert 50. The insert has a horseshoe shape and is configured to fit between the femur and tibia as a tibial prosthesis in a patient, integrate with surrounding bone, and remain in position without the use of any bone cement.

The insert generally has a flat configuration defined by an outer planar surface or bone engaging surface 52 and an inner planar surface or articulating surface 54. The inner and outer surfaces define a shell wall 56. The outer surface can also have a projected stem or pegs anchoring into the tibia to enhance fixation. As discussed with reference to the proximal body in FIG. 1, the outer surface (or bone engaging surface) is porous or textured 58.

It is important to note that the outer surface 52 directly contacts and engages bone. As such, a separate tibial tray is not required. Such trays are typically constructed of titanium alloy or cobalt-chromium alloy and have a porous coating on the external surface to engage bone. By contrast, the bone engaging or outer surface 52 is textured or porous 58; and such a separate tibial tray is not needed. The inner surface 54 is adapted to serve as the articulating surface and thus receives the femoral condyles (not shown) of a knee prosthesis.

Preferably, the polymeric components of the present invention are formed from ultra high molecular weight polyethylene, UHMWPE, specified by ASTM F 648. The UHMWPE has less than about 60% crystallinity, less than about 290 .ANG. lamellar thickness, and less than about 940 MPa tensile elastic modulus (so as to reduce production of fine particles from the prosthesis during wear). Such UHMWPE is taught in U.S. Pat. No. 5,879,400 entitled "Melt-irradiated ultra high molecular weight polyethylene prosthetic devices" to Merrill et al.; this patent being incorporated by reference herein.

As one important advantage of the present invention, the textured or porous surface is not applied as a coating to the prosthesis or fabricated during the formation of the polymer or polymeric structure. Rather, any one of or combination of several surface texturing techniques is used to form the textured or porous surface. These techniques include grit blasting, laser texturing, and machining (such as cutting, drilling, knurling, milling, and combinations of these techniques).

Figure 7:
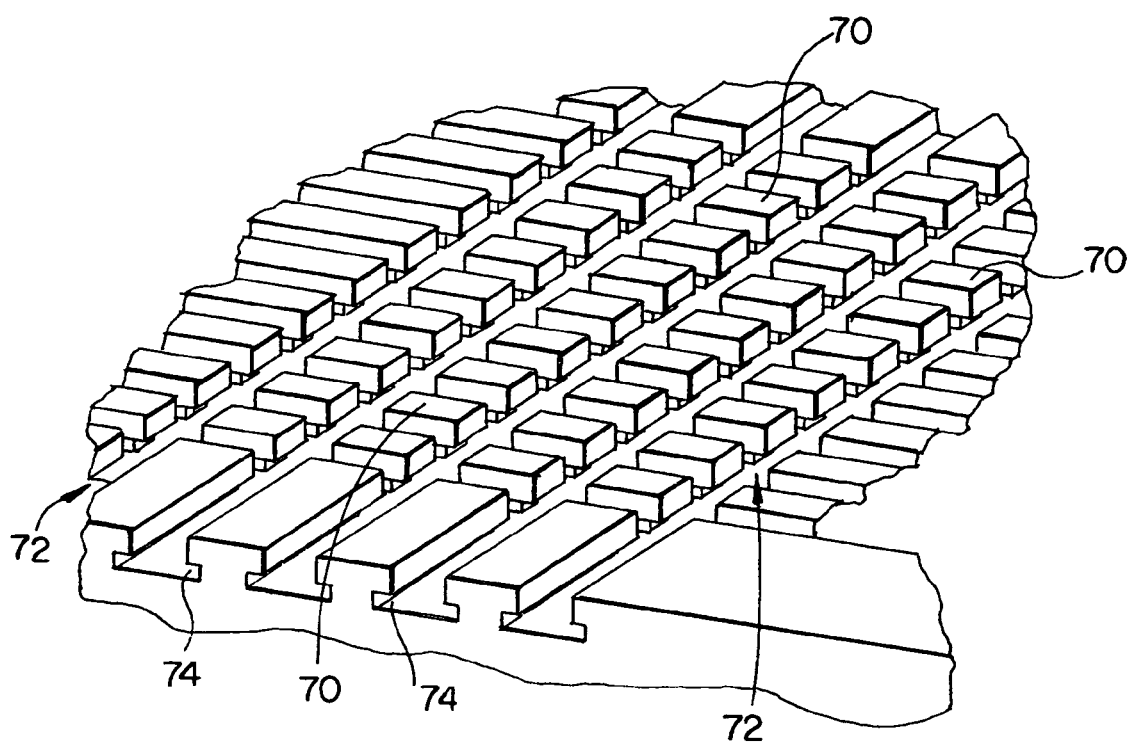
FIG. 7 is an illustration of a polymeric textured surface created from a key-way cutter.

FIG. 7 shows an example of a machining technique to create a textured or porous surface on a polymer. Here a key-way cutter is used to create a series of bosses 70 forming a grid of numerous columns and rows. The bosses on the surface result from numerous passes of the key-way cutter in two intersecting directions. The key-way cutter leaves channels 72 adjacent each boss and undercuts 74 under each boss. The undercuts 74 provide a foothold or anchor location into which bone and tissue are able to grow.

A textured or porous polyethylene surface may also be formed using a grit blasting technique. The surface will become porous after it is subjected to grit blasting using either aluminum oxide particles or glass beads. Grit blasting techniques and methods of operation are widely known to those skilled in the art.

Laser texturing is particularly advantageous because an array of pores in various sizes, orientations, and thickness can be created. For example, the diameter, intensity, and angle of drilling or penetration of the laser beam can be altered to change the geometry of the porous or textured surface. Multiple passes over the surface with the laser can be used to achieve the required arrays of pores or porous structure.

The porous surface layer can also be coated, doped, or the like with another media to enhance bone bonding properties between the prosthesis and surrounding bone. Plasma sprayed titanium, hydroxyapatite, or growth agents (such as BMPs), for example, can be added or applied to the surface.

Another important advantage of the present invention is that the prosthesis is formed of a polymer. As such, the elastic modulus of the implant more closely matches the natural elastic modulus of surrounding bone. The likelihood or amount of bone resorption is thus reduced, especially when compared to traditional implants formed entirely of titanium or other metals.

The porous or textured surface of the present invention has other advantages as well. These advantages include:

The porous or textured surface layer can be fabricated on the backside of articulating ultra-high-molecular-weight polyethylene inserts. These inserts can directly interface with bone without the usage of a metal backing or support. In contrast, the components made of as-fabricated porous polymer will be less advantageous in this type of application.

The porous or textured surface can be made as polymeric pads that are easily shaped. The pads can be used to fill spaces between implants and bone.

No sintering process is needed to produce the porous or textured surface. As such, the mechanical and fatigue properties of the implant are maintained and not altered.

The porous or textured surface is integrated with the bulk or prosthetic component. As such, there is no threat or likelihood about the outer surface detaching from the bulk or prosthetic component.

Although illustrative embodiments have been shown and described, a wide range of modifications, changes, and substitutions is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A prosthetic femoral hip stem, comprising:
    a metal core having an elongated body extending from a proximal portion to a distal portion, the distal portion adapted to be inserted into an intramedullary canal of a patient; and
    a proximal body connected to the proximal portion, the proximal body having a distal end surface and a proximal end surface, and wherein the proximal body completely surrounds the metal core between the distal end surface and the proximal end surface, the proximal body being formed entirely of polymer and having an external surface adapted to engage bone in the intramedullary canal, wherein the external surface is textured such that the external surface has a multitude of pores adapted to induce growth of cancellous and cortical bone into the external surface, and further wherein the external surface of the proximal body is configured and arranged to make direct contact with the cancellous and cortical bone without cement between the bone and the external surface of the proximal body, and still further wherein the external surface has a textured thickness from about 0.05 mm to about 5 mm.

2. The prosthetic femoral hip stem as defined in claim 1 wherein the pores have an average pore diameter from about 40 µm to about 1000 µm.

3. The prosthetic femoral hip stem as defined in claim 2 wherein the pores have a porosity ranging from about 40% to about 65%.

4. The prosthetic femoral hip stem as defined in claim 3 wherein the pores have interconnections with an average diameter of greater than about 50 microns.

5. The prosthetic femoral hip stem as defined in claim 1 wherein the pores are coated with one of plasma sprayed titanium or hydroxyapatite.

6. The prosthetic femoral hip stem as defined in claim 1, wherein the proximal body has a series of bosses forming a grid of numerous columns and rows, and further wherein each boss has an undercut adapted to receive bone growth.

7. A femoral hip stem, comprising:
a metal core having an elongated body extending from a proximal portion to a distal portion, the distal portion adapted to be inserted into a intramedullary canal of a patient; and
a proximal body connected to the proximal portion, the proximal body having a distal end surface and a proximal end surface, and wherein the proximal body completely surrounds the metal core between the distal end surface and the proximal end surface, the proximal body formed of polymer with an external surface adapted to engage bone in the intramedullary canal, wherein the external surface is texturized such that the external surface has an array of pores adapted to encourage bone growth into the external surface, and further wherein the external surface of the proximal body is configured and arranged to make direct contact with the cancellous and cortical bone without cement between the bone and the external surface of the proximal body, and still further wherein at least a portion of the core, distal of said proximal body, is not covered by the proximal body.

8. The femoral hip stem as defined in claim 7 wherein the proximal body is formed of ultra high molecular weight polyethylene.

9. The femoral hip stem as defined in claim 8 wherein the proximal body has a tensile elastic modulus of less than about 940 MPa.

10. The femoral hip stem as defined in claim 8 wherein the array of pores covers substantially all of the external surface.

11. A femoral hip stem, comprising:
a core having an elongated body extending from a proximal portion to a distal portion, the distal portion adapted to be inserted into a intramedullary canal of a patient; and
a proximal body connected to the proximal portion, the proximal body having a distal end surface and a proximal end surface, and wherein the proximal body substantially surrounds the core between the distal end surface and the proximal end surface, the proximal body formed of polymer with an external surface adapted to engage bone in the intramedullary canal, wherein the external surface is texturized such that the external surface has an array of pores adapted to encourage bone growth into the external surface, wherein the proximal body has a series of bosses forming a grid of numerous columns and rows, and wherein each boss has an undercut adapted to receive bone growth.

12. A femoral hip stem, comprising:
a metal core having an elongated body extending from a proximal portion to a distal portion, the distal portion adapted to be inserted into a intramedullary canal of a patient; and
a proximal body connected to the proximal portion, the proximal body having a distal end surface and a proximal end surface, and wherein the proximal body completely surrounds the metal core between the distal end surface and the proximal end surface, the proximal body formed of polymer with an external surface adapted to engage bone in the intramedullary canal, wherein the external surface is texturized such that the external surface has an array of pores adapted to encourage bone growth into the external surface, and further wherein the external surface of the proximal body is configured and arranged to make direct contact with the cancellous and cortical bone without cement between the bone and the external surface of the proximal body,
wherein the proximal body is formed of ultra high molecular weight polyethylene;
wherein the array of pores covers substantially all of the external surface; and
wherein the external surface has a textured thickness from about 0.05 mm to about 5 mm.

13. The femoral hip stem as defined in claim 12 wherein the pores have an average pore diameter from about 40 $\mu$m to about 1000 $\mu$m.

14. The femoral hip stem as defined in claim 13 wherein the pores have a porosity ranging from about 40% to about 65%.

15. A prosthetic femoral hip stem, comprising:
a core having an elongated body extending from a proximal portion to a distal portion, the distal portion adapted to be inserted into an intramedullary canal of a patient; and
a proximal body connected to the proximal portion, the proximal body having a distal end surface and a proximal end surface, and wherein the proximal body completely surrounds the core between the distal end surface and the proximal end surface, the proximal body being formed entirely of polymer and having an external surface adapted to engage surrounding bone, wherein the external surface is textured; and
wherein at least a portion of the core, distal of the proximal body, is not covered by the proximal body.

16. The prosthetic femoral hip stem as defined in claim 15, wherein the core is metal.

17. The prosthetic femoral hip stem as defined in claim 15, wherein the external surface of the proximal body is configured and arranged to make direct contact with the surrounding bone without cement between the bone and the external surface of the proximal body.

18. The prosthetic femoral hip stem as defined in claim 15, wherein the proximal body has a series of bosses forming a grid of numerous columns and rows, and further wherein each boss has an undercut adapted to receive bone growth.

19. A prosthetic femoral hip stem, comprising:
a metal core having an elongated body extending from a proximal portion to a distal portion, the distal portion adapted to be inserted into an intramedullary canal of a patient; and
a proximal body connected to the proximal portion, the proximal body having a distal end surface and a proximal end surface, and wherein the proximal body completely surrounds the metal core between the distal end surface and the proximal end surface, the proximal body being formed entirely of polymer and having an external surface adapted to engage bone in the intramedullary canal, wherein the external surface is textured such that the external surface has a multitude of pores adapted to induce growth of cancellous and cortical bone into the external surface, and further wherein the external surface of the proximal body is configured and arranged to make direct contact with the cancellous and cortical bone without cement between the bone and the external surface of the proximal body; wherein at least a portion of the core, distal of said proximal body, is not covered by the proximal body.

* * * * *